United States Patent [19]

Steffens

[11] 4,382,814

[45] May 10, 1983

[54] HERBICIDAL DERIVATIVES OF 5-PHENOXY-2-NITROFURAN-3-CARBOXYLIC ACID

[75] Inventor: James J. Steffens, Yardley, Pa.

[73] Assignee: Rhone-Poulenc Agrochimie, Lyons, France

[21] Appl. No.: 286,931

[22] Filed: Jul. 27, 1981

[51] Int. Cl.³ ............... A01N 43/08; C07D 307/68
[52] U.S. Cl. .................................. 71/88; 549/479
[58] Field of Search .......................... 549/479; 71/88

[56] References Cited

U.S. PATENT DOCUMENTS

| | | | |
|---|---|---|---|
| 3,682,968 | 8/1972 | Shen et al. | 549/479 |
| 3,784,635 | 1/1974 | Theissen | 560/21 |
| 3,907,866 | 9/1975 | Theissen | 560/21 |
| 4,063,929 | 12/1977 | Bayer et al. | 71/115 |

FOREIGN PATENT DOCUMENTS 21692 1/1981 European Pat. Off. .
49-62637 6/1974 Japan .

OTHER PUBLICATIONS

H. Gilman et al., Orientation in the Furan Nucleus. VI. β-Substituted Furans, J. Am. Chem. Soc. vol. 55, pp. 2903–2909 (1933).

*Primary Examiner*—Richard Raymond
*Attorney, Agent, or Firm*—Morgan, Finnegan, Pine, Foley & Lee

[57] ABSTRACT

There are provided herbicidal derivatives of 5-phenoxy-2-nitrofuran-3-carboxylic acid.

5 Claims, No Drawings

HERBICIDAL DERIVATIVES OF 5-PHENOXY-2-NITROFURAN-3-CARBOXYLIC ACID

BACKGROUND OF THE INVENTION

Herbicidal 5-[2-chloro-4-(trifluoromethyl)phenoxy]-2-nitrobenzoic acid and salts thereof, and various herbicidal derivatives of these compounds have been proposed including alkyl and cycloalkyl esters, alkylthio esters, phenyl ester, alkyl and dialkyl amido and benzoyl chloride forms. U.S. Patents which describe such compounds and the like include U.S. Pat. Nos. 3,652,645; 3,784,635; 3,873,302; 3,983,168; 3,907,866; 3,798,276; 3,928,416; and 4,063,929.

SUMMARY OF THE INVENTION

This invention provides certain herbicidal compounds of the formula:

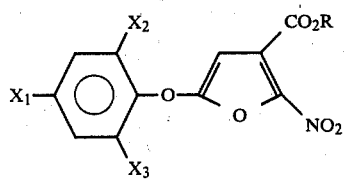

where
(i) R is alkyl (substituted or unsubstituted, e.g., having including substituents, from 1 to 12 carbon atoms); and
(ii) $X_1$, $X_2$ and $X_3$ are groups which are capable of being incorporated into formula I and which collectively impart herbicidal activity thereto.

Examples of the groups $X_1$, $X_2$, $X_3$ and R are as follows:

$X_1$ and $X_2$ may be the same or different and may be selected from the group consisting of halo (e.g., Cl, Br or F), nitro, cyano, and trihalomethyl (e.g., $CF_3$);

$X_3$ may be hydrogen or any of the groups exemplified above for $X_1$ and $X_2$; and R may be $C_1$–$C_5$ alkyl which is unsubstituted or substituted with at least one group selected from the group consisting of hydroxy, alkoxy, halo (e.g., Cl, Br or F), alkylthio and alkoxycarbonyl (i.e., COO alkyl).

A preferred compound according to Formula I is:

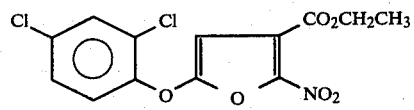

The following compound was prepared:

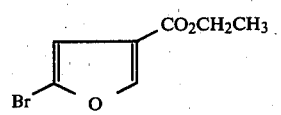

Ethyl 2-bromo-4-furoate was prepared by bromination of ethyl 3-furoate using the method of H. Gilman and R. R. Burtner, *J. Am. Chem. Soc.* 55, 2903(1033). The product was purified by distillation.

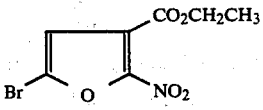

Ethyl 5-bromo-2-nitro-3-furoate, II may be prepared by nitration of I using the method of Gilman and Burtner, op cit. The product is purified by crystallization from a suitable solvent.

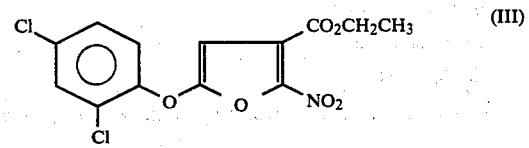

III may be prepared from II and sodium 2,4-dichlorophenoxide in anhydrous DMF at a suitable temperature, e.g., 25°–150° C.

The compounds of this invention can be applied in various ways to achieve herbicidal action. They can be applied per se, but may be applied as the toxic components in pesticidal compositions of the compound and a carrier. These compositions may be applied directly to the soil and often incorporated therewith. The compositions can be applied as granulars or dusts; as liquid sprays, or as gas-propelled sprays and can contain, in addition to a carrier, additives such as emulsifying agents, binding agents, gases compressed to the liquid state, odorants, stabilizers, and the like. A wide variety of liquid and solid carriers can be used. Non-limiting examples of solid carriers include talc, bentonite, diatomaceous earth, pyrophyllite, fullers earth, gypsum, flours derived from cotton seeds and nut shells, and various natural and synthetic clays having a pH not exceeding about 9.5. Non-limiting examples of liquid carriers include water, organic solvents such as alcohols, ketones, light oils, and medium oils and vegetable oils such as cottonseed oil. In practice, herbicidal application is measured in terms of pounds of herbicide applied per acre. The compounds of this invention are effective herbicides when applied in herbicidal amounts, e.g., at rates between about 0.03 pound and about 10 pounds per acre.

Although the present invention has been described with preferred embodiments, it is to be understood that modifications and variations may be resorted to, without departing from the spirit and scope of this invention, as those skilled in the art will readily understand. Such modifications and variations are considered to be within the purview and scope of the appended claims.

What is claimed is:

1. A herbicidal compound of the formula

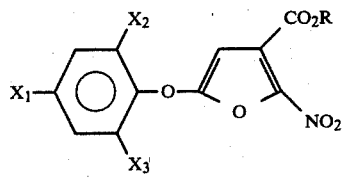

where
(i) R is a $C_1$ to $C_5$ alkyl which is unsubstituted or substituted with at least one substituent selected from the group consisting of hydroxy, alkoxy, halo alkythio, and alkoxycarbonyl;

(ii) $X_1$ and $X_2$ are the same or different and are selected from the group consisting of halo, nitro, cyano, and trihalomethyl; and (iii) $X_3$ is selected from the group consisting of hydrogen, halo, nitro, cyano, and trihalomethyl.

2. A compound according to claim 1 wherein (i) X is $CF_3$ or Cl;

(ii) $X_2$ is Cl; and (iii) $X_3$ is H.

3. A compound according to claim 1 of the formula

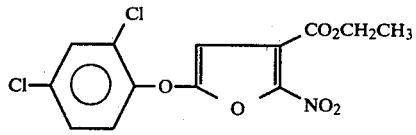

4. A herbicidal composition comprising a herbicidally effective amount of a compound according to any one of claims 1, 2, or 3 and an agronomically acceptable carrier.

5. A method for combating unwanted plants which comprises contacting them with a herbicidally effective amount of a compound according to any one of claims 1, 2, or 3.

* * * * *